United States Patent [19]

Hilty

[11] Patent Number: 4,898,956

[45] Date of Patent: Feb. 6, 1990

[54] METHOD TO PREPARE THERMO-OXIDATIVELY STABLE PHENYLMETHYLSILOXANE FLUIDS

[75] Inventor: Terrence K. Hilty, Midland County, Mich.

[73] Assignee: Dow Corning Corporation, Midland, Mich.

[21] Appl. No.: 372,495

[22] Filed: Jun. 27, 1989

[51] Int. Cl.$^4$ .............................. C07F 7/08; C07F 7/18
[52] U.S. Cl. ..................................................... 556/401
[58] Field of Search ........................................ 556/401

[56] References Cited

U.S. PATENT DOCUMENTS

| | | | |
|---|---|---|---|
| 2,658,882 | 11/1953 | Maneri | 260/37 |
| 3,002,989 | 10/1961 | Awe et al. | 260/448.2 |
| 3,321,501 | 5/1967 | Wilkus et al. | 260/429 |
| 3,745,129 | 7/1973 | Brown et al. | 252/49.7 |
| 4,070,343 | 1/1978 | Kishimoto et al. | 260/45.75 P |
| 4,122,109 | 10/1978 | Halm | 260/448.23 |
| 4,193,885 | 3/1980 | Holm | 252/78.3 |
| 4,560,784 | 12/1985 | Mori et al. | 556/401 |
| 4,637,889 | 1/1987 | Kishimoto et al. | 252/75 |

Primary Examiner—Paul F. Shaver
Attorney, Agent, or Firm—Robert L. McKellar

[57] ABSTRACT

Thermo-oxidatively stable polysiloxanes are prepared by adding certain zirconium compounds to the fluid. These zirconium compounds are of the organozirconium or siloxyzirconium types. Two methods for preparation of the fluids is discussed. The fluids of this invention are useful as heat transfer fluids, lubricants, or damping fluids. They have particular usefulness in applications that have a low surface area to volume ratio.

21 Claims, No Drawings

METHOD TO PREPARE THERMO-OXIDATIVELY STABLE PHENYLMETHYLSILOXANE FLUIDS

The invention relates to phenylmethylsiloxanes that have improved thermal stability in moisture and oxygen containing environments. This stability is enhanced by the use of certain zirconium compounds that are blended in the presence of heat with the phenylmethylsiloxane fluids or a zirconium modified polysiloxane fluid that is compatible with and is blendable with the desired phenylmethylsiloxane fluids. The fluids of this invention are useful as heat transfer fluids, lubricants and damping fluids.

BACKGROUND OF THE INVENTION

Polysiloxane fluids, particularly those with methyl functionality on the siloxane backbone, are known in the art to be unstable in the presence of oxygen at high temperatures. Oxygen, when present, is known to enter into the fluid by diffusion; therefore all contain a gradient of oxygen content and may gel preferentially at the surface. The inventor theorizes, but should not be held to the belief that the mechanism resulting in the instability is as follows:

It is believed that in the presence of oxygen the following reaction (I) occurs producing a silanol and formaldehyde.

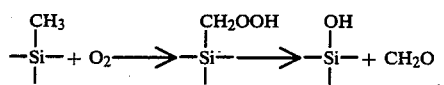

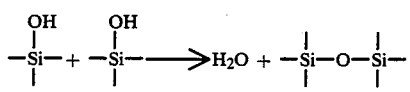

The silanol groups, thus formed, can further undergo a reaction (II) to produce water and high molecular weight polysiloxanes or gels. These reactions appear to be significantly inhibited when aryl groups, such as phenyl, are contained on the silicon in place of the aliphatic chains.

Another primary mechanism of thermal degradatons in siloxane fluids is that of "backbiting". Backbiting in siloxane fluids is illustrated in equation (III).

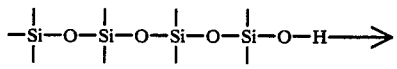

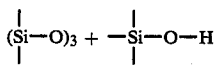

In this process the molecular weight of the polymer decreases and under high temperature low molecular weight cyclics are vaporized.

Using zirconium and other metal compounds to stabilize organopolysiloxanes used in high temperature applications has been shown in the prior art. The inventor speculates that these compounds add stability by inhibiting the reaction described by I-III above. U.S. Pat. No. 4,122,109 to Halm shows a method of preparing methylpolysiloxanes with improved stability using Ti, Zr, or Hf compounds or their decomposition products. However these materials were tested and found useful only in non-oxidative, anhydrous environments. Kishimoto et al., U.S. Pat. No. 4,637,889 teaches a mixture of an organopolysiloxane, a zirconium-containing organopolysiloxane and a cerium-containing organopolysiloxane for use as coupler fluids. This invention is dependent on synergism of both the cerium and zirconium additives to provide the desired stability.

Zirconium compounds have also been shown in prior art to be useful in improving the stability of silicone rubbers. For example U.S. Pat. No. 2,658,882 to Maneri teaches a silicone rubber that resists deterioration of physical properties at 150 to 250 degrees Celsius by the addition of metallic zirconates, metallic fluorozirconates and zirconium silicates into the unvulcanized silicone rubber composition.

The use of metallocenes, especially ferrocene, to improve thermal stability in organopolysiloxanes is also well known in the art. For example, Awe et al., U.S. Pat. No. 3,002,989 shows a method for preparing siloxane fluids for use in high temperature applications by the addition of a ferrocene compound. This process requires a pre-oxidation step at temperatures from 450 to 600 degrees Fahrenheit. Brown et al., U.S. Pat. No. 3,745,129 shows the use of polymeric silylorganoferrocenes for improving the stability of organopolysiloxanes. However the process for making the polymeric silylorganoferrocenes is complex and solubility of the polymeric silylorganoferrocenes in the organopolysiloxane was not always readily achieved.

From the prior art, it was not obvious to use the specific metallocenes and organometallic compounds of this invention to stabilize phenylmethylsiloxanes in a thermal oxidative environment.

It is an object of this invention to provide phenylmethylsiloxane fluids which show improved thermal stability in oxygen and moisture containing environments.

It is a further object of this invention to provide a simplified method for making thermo-oxidatively stable phenylmethylsiloxanes using certain zirconium additives.

It is a further object of this invention to show the improved performance of the phenylmethylsiloxane fluids stabilized with zirconium in low surface area to volume applications.

THE INVENTION

The present invention relates to phenylmethylsiloxane fluids that are stabilized by the addition of certain zirconium compounds. It is believed that these zirconium compounds undergo a decomposition reaction in the process of blending it with the phenylmethylsiloxane fluid in the presence of heat. The structure of the resulting zirconium compound is not known at this time therefore the mechanism for improving the stability of the phenylmethylsiloxane fluid is also not known at this time.

The phenylmethylsiloxane fluids applicable in this invention are commercially available and are of the general formula:

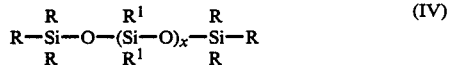

(IV)

where each R is independently selected from an alkyl group having 1 to 6 carbons and an aryl group having 5 to 10 carbons, each $R^1$ is selected from phenyl or methyl groups, with the proviso that they are not all methyl and x equals 3 to 100.

The preferred structure of the molecule is where R is methyl and $R^1$ is selected from phenyl groups or methyl groups. The preferred range for x equals 5 to 25.

The stabilized zirconium modified fluid is produced from the organozirconium or siloxy-zirconium compound that is heated in the presence of the phenylmethylsiloxane fluid or the polysiloxane fluid which is compatible and blendable with the phenylmethylsiloxane fluid. The blend of organozirconium or siloxy-zirconium compound and the polysiloxane or phenylmethylsiloxane fluid should be held at a temperature from 220 to 400 degrees Celsius for a period of at least 24 hours. Cold blending of the organozirconium compound with the phenylmethylsiloxane or polysiloxane fluid to produce the zirconium modified fluid does not appear to work due to incompatibility of the two substances.

Organozirconium compounds of particular usefulness in this invention are those containing organic groups which may contain atoms of hydrogen, oxygen, or carbon. Examples of suitable organic groups include saturated or unsaturated hydrocarbons, esters, and alcohols. Organozirconium compounds of particular usefulness in this invention are zirconium octoate and dimethyl zirconocene.

The siloxy-zirconium compounds useful in this invention are of the general formula $R^2_a Zr(OSiR^3_b R^4_{3-b})_{4-a}$ where $R^2$ is an alkyl group of 1 to 6 carbons or an aryl group of 5 to 10 carbons, $R^3$ is an alkyl group of 1 to 6 carbons, $R^4$ is an aryl group of 5 to 10 carbons, a equals 0 to 2 and b equals 0 to 3. The preferred structure is where $R^2$ is cyclopentadienyl, $R^3$ is methyl and $R^4$ is phenyl.

The siloxy-zirconium compounds useful in this invention can be prepared by methods known in the art or by reacting dimethyl zirconocene with a silanol of the formula $R^3_b R^4_{3-b} SiOH$ where $R^3$, $R_4$ and b are as previously described.

The process for producing a thermo-oxidatively stable phenylmethylsiloxane comprises:

(1) blending the organozirconium or siloxy-zirconium compound with the phenylmethylsiloxane of formula IV at levels of 250 ppm to 5000 ppm zirconium, heating to 220 to 400 Celsius for a period of at least 24 hours and cooling to room temperature or (2) blending the organozirconium or siloxy-zirconium compound with the compatible polysiloxane fluid at levels of 250 ppm to 5 percent by weight zirconium, heating to 220 to 400 Celsius for a period of at least 24 hours, cooling to room temperature and then cold blending with the desired phenylmethylsiloxane fluid at levels to provide 250 ppm to 5000 ppm zirconium in the fluid.

It is believed that the zirconium compound reacts with the silanols initially present or generated during thermal oxidation in the phenylmethylsiloxane fluid which imparts stability. Therefore it is believed that the concentration of zirconium metal necessary to impart stability is proportional to the concentration of silanol present in the fluid. However this may not be true at extremely low or high levels of silanol. The preferred levels of this invention are 250 parts zirconium metal per million parts phenylmethylsiloxane to 5000 parts zirconium metal per million parts phenylmethylsiloxane.

Although this invention may be useful in any application requiring a stable polysiloxane in an oxidative environment it appears to be particularly useful in applications that have a low surface area to volume ratios. The siloxanes of this invention are useful as heat transfer fluids, lubricants or damping fluids. Particularly those applied in moisture or oxygen containing environments or where there is a low surface area to volume ratio.

So that those skilled in the art can understand and appreciate the invention taught herein, the following examples are presented, it being understood that these examples should not be used to limit the scope of this invention over the limitations found in the claims attached hereto.

EXAMPLE 1

38.46 g of a phenylmethylsiloxane fluid of the formula

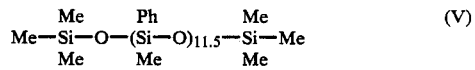

(V)

(Ph equals phenyl and Me equals methyl) and 10.17 g of 6% zirconium octoate in mineral spirits were loaded into a flask equipped with a heating mantle, magnetic stirrer, thermometer and distillation head. The mixture was heated to 275 degrees Celsius to drive off the mineral spirits. The temperature was then raised to 300 degrees Celsius and held for 24 hours. The mixture was allowed to cool to room temperature. 37.58 g of zirconium modified phenylmethylsiloxane fluid was recovered.

Sample 1 was prepared by adding 5.26 g of the above mixture to 100.10 g of a phenylmethylsiloxane fluid of the formula V. (Zirconium level of 1054 ppm). A second sample was prepared by adding 11.11 g of the zirconium mixture produced above to 100.00 g of the phenylmethylsiloxane fluid of formula V. (Zirconium level of 2041 ppm)

The above 2 samples and a blank containing only the phenylmethylsiloxane fluid were tested for stability in an oxygen and moisture containing environment. The tests were conducted in a system consisting of an aluminum block having four holes, 7 inches deep, bored into the top surface. Temperature of the aluminum block was maintained by placing the block on a heating mantle held at 300 degrees Celsius by a proportional controller. Samples were placed in 15 ml unwashed glass bottles having a diameter of 2.3 cm and a fluid height of 4 cm. The surface area to volume ratio was calculated to be 0.25. The bottles were placed into the holes of the aluminum block and were not capped or sealed in any manner.

Thermo-oxidative testing resulted in the blank gelling at 330 hours, sample 1 gelling at 466 hours and sample 2 gelling at 498 hours. The magnitude of improvement can be expressed with a term referred to as the stability factor, St, the ratio of the gelation time for the fluid containing the additive divided by the time required for the blank fluid to gel. St for samples 1 and 2 were 1.35 and 1.51 respectively. Thus, in this instance, doubling the Zr content increased the St factor by an additional 12 percent.

EXAMPLE 2

Sample 3 was prepared by adding 125 g of a phenylmethylsiloxane of formula V and 0.34 g of dimethyl zirconocene into an inert flask equipped with a magnetic stirrer, heating mantle, Claisen head, thermometer, condenser, dry ice trap and oil bubbler. The flask contents were heated to 300 degrees Celsius and held under reflux for 24 hours. Contents were cooled to room temperature and zirconium level was determined to be 1375 ppm.

Thermo-oxidative testing using the method described in example 1 of sample 3 and a blank containing only phenylmethylsiloxane fluid resulted in the blank gelling in 311 hours and sample 3 gelling in 710 hours. The stability factor for sample 3 is 2.28.

EXAMPLE 3—COMPARATIVE

Sample A was prepared using a polysiloxane of formula V an dimethyl zirconocene by the method described in Example 2 so that the Zr content was 200 (±69) ppm.

Sample B was prepared by the same method used to prepare sample A using a polysiloxane of formula V and iron octoate so that the Fe content was 150 ppm.

Sample C consisted only of the phenylmethylsiloxane fluid of formula V.

Samples A, B and C were then tested for thermal stability in the method described in example 1 except 150 ml beakers were used in place of the 15 ml vial and testing was done in a Dispatch air circulating oven. Samples with surface area to volume ratios of 0.23, 0.29, 0.43, 0.54, 0.65, and 1.17 were tested at 300 degrees Celsius.

Results of the studies are given in Table 1. It can be concluded by the comparison of stability factors and gelation times that there is a significant improvement with the dimethyl zirconocene at the lower surface area to volume ratios relative to the sample enhanced with iron octoate.

TABLE

| Surface Area/ Volume | Gelation Time (hrs.) | | | Stability Factors | |
|---|---|---|---|---|---|
| | A | B | C | A | B |
| 0.23 | 899 | 572 | 426 | 2.11 | 1.34 |
| 0.29 | 791 | 596 | 384 | 2.06 | 1.55 |
| 0.43 | 621.5 | 596 | 360 | 1.73 | 1.73 |
| 0.54 | 508 | 668 | 282 | 1.80 | 2.37 |
| 0.65 | 460 | 788 | 215 | 2.14 | 3.67 |
| 1.17 | 364 | 1032.5 | 168 | 2.17 | 6.15 |

What is claimed is:

1. A polysiloxane fluid consisting essentially of
(i) a polysiloxane of the formula

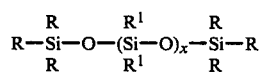

where each R is independently selected from an alkyl group having 1 to 6 carbons and an aryl group having 5 to 10 carbons; each $R^1$ is independently selected from phenyl and methyl groups, with the proviso that they are not all methyl; and x equals 3 to 100 and,
(ii) an organozirconium compound.

2. A fluid as in claim 1 where the polysiloxane is

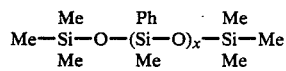

where Ph represents the phenyl group, Me represents the methyl group and x is equal to 3 to 25.

3. A fluid as in claim 1 where the polysiloxane is

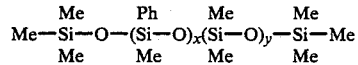

where Ph represents the phenyl group, Me represents the methyl group, x is greater than 2, y is an integer and the sum of x+y is less than 100.

4. A fluid as in claim 1 where the organozirconium compound is selected from a group consisting essentially of dimethyl zirconocene and zirconium octoate.

5. A fluid as in claim 1 where the organozirconium compound is present at levels from 250 parts zirconium metal per million parts polysiloxane to 5000 parts zirconium metal per million parts polysiloxane.

6. A polysiloxane fluid consisting essentially of
(i) a polysiloxane of the formula

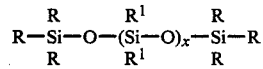

where each R is independently selected from an alkyl group having 1 to 6 carbons and an aryl group having 5 to 10 carbons; each $R^1$ is independently selected from phenyl and methyl groups, with the proviso that they are not all methyl; and x equals 3 to 100 and,
(ii) a siloxy-zirconium compound.

7. A fluid as in claim 6 where the polysiloxane is

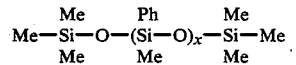

where Ph represents the phenyl group, Me represents the methyl group and x is equal to 3 to 25.

8. A fluid as in claim 6 where the polysiloxane is

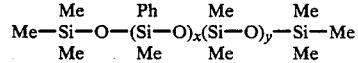

where Ph represents the phenyl group, Me represents the methyl group, x is greater than 2, y is an integer and the sum of x+y is less than 100.

9. A fluid as in claim 6 where the siloxy-zirconium compound is of the formula $Cp_aZr(OSiR^3{}_bR^4{}_{3-b})_{4-a}$ where Cp represents the cyclopentadienyl group, $R^3$ is methyl, $R^4$ is phenyl, a equals 0 to 2 and b equals 0 to 3.

10. A fluid as in claim 6 where the siloxy-zirconium compound is present at levels from 250 parts zirconium metal per million parts polysiloxane to 5000 parts zirconium metal per million parts polysiloxane.

11. A process for preparing polysiloxane fluids having improved thermo-oxidative stability consisting essentially of
(A) mixing components consisting essentially of
(i) a polysiloxane of the formula

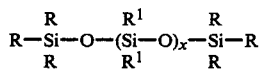

where each R is independently selected from an alkyl group having 1 to 6 carbons and an aryl group having 5 to 10 carbons; each $R^1$ is independently selected from phenyl and methyl groups, with the proviso that they are not all methyl; and x equals 3 to 100 and,
(ii) a component selected from an organozirconium compound or a siloxy-zirconium compound in sufficient amounts to provide 250 to 5000 parts zirconium per million parts fluid and,
(B) Heating the mixture of (A) to temperatures of 220 to 400 degrees Celsius.

12. A process as in claim 11 where the polysiloxane is

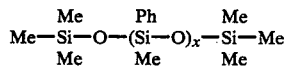

where Ph represents the phenyl group, Me represents the methyl group and x is equal to 3 to 25.

13. A process as in claim 11 where the polysiloxane is

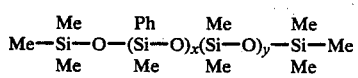

where Ph represents the phenyl group, Me represents the methyl group, x is greater than 2, y is an integer and the sum of x+y is less than 100.

14. A process as in claim 11 where the organozirconium compound is selected from a group consisting essentially of dimethyl zirconocene and zirconium octoate.

15. A process as in claim 11 where the siloxy-zirconium compound is of the formula $Cp_aZr(OSiR^3{}_bR^4{}_{3-b})_{4-a}$ where Cp represents the cyclopentadienyl group, $R^3$ is methyl, $R^4$ is phenyl, a equals 0 to 2 and b equals 0 to 3.

16. A process for preparing polysiloxane fluids having improved thermo-oxidative stability consisting essentially of
(A) mixing components consisting essentially of
(i) a polysiloxane that is compatible and blendable with a phenyl containing polysiloxane of the formula

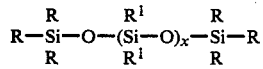

where each R is independently selected from an alkyl group having 1 to 6 carbons and an aryl group having 5 to 10 carbons; each $R^1$ is independently selected from phenyl and methyl groups, with the proviso that they are not all methyl; and x equals 3 to 100 and,
(ii) a component selected from an organozirconium compound or a siloxy-zirconium compound in sufficient amounts to provide 250 to 5,000 parts zirconium per million parts fluid,
(B) Heating the mixture of (A) to temperatures of 220 to 400 degrees Celsius and,
(C) Blending the mixture of (B) with said phenyl containing polysiloxane fluid in sufficient quantities so that there is 250 to 5000 parts zirconium per million parts the polysiloxane fluid.

17. A process as in claim 16 where the phenyl containing polysiloxane is

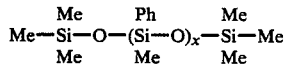

where Ph represents the phenyl group, Me represents the methyl group and x is equal to 3 to 25.

18. A process as in claim 16 where the phenyl containing polysiloxane is

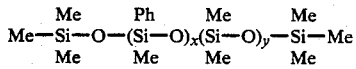

where Ph represents the phenyl group, Me represents the methyl group, x is greater than 2, y is an integer and the sum of x+y is less than 100.

19. A process as in claim 16 where the polysiloxane and phenyl containing polysiloxane are the same.

20. A process as in claim 16 where the organozirconium compound is selected from a group consisting essentially of dimethyl zirconocene and zirconium octoate.

21. A process as in claim 16 where the siloxy-zirconium compound is of the formula $Cp_aZr(OSiR^3{}_bR^4{}_{3-b})_{4-a}$ where Cp represents the cyclopentadienyl group, $R^3$ is methyl, $R^4$ is phenyl, a equals 0 to 2 and b equals 0 to 3.

* * * * *